United States Patent
Poland

(10) Patent No.: US 9,353,026 B2
(45) Date of Patent: May 31, 2016

(54) OIL SOLUBLE HYDROGEN SULFIDE SCAVENGER

(71) Applicant: BAKER HUGHES INCORPORATED, Houston, TX (US)

(72) Inventor: Ross Poland, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 52 days.

(21) Appl. No.: 13/946,836

(22) Filed: Jul. 19, 2013

(65) Prior Publication Data

US 2015/0025258 A1 Jan. 22, 2015

(51) Int. Cl.
*C07C 7/173* (2006.01)
*C07C 7/148* (2006.01)
*C07F 3/06* (2006.01)
*C10M 141/08* (2006.01)
*C10G 29/16* (2006.01)

(52) U.S. Cl.
CPC ........... *C07C 7/14875* (2013.01); *C07C 7/1485* (2013.01); *C07C 7/173* (2013.01); *C07F 3/06* (2013.01); *C10G 29/16* (2013.01); *C10G 2300/207* (2013.01); *C10M 141/08* (2013.01)

(58) Field of Classification Search
None
See application file for complete search history.

(56) References Cited

U.S. PATENT DOCUMENTS

| | | | |
|---|---|---|---|
| 2,584,041 A * | 1/1952 | Nowak et al. | 530/230 |
| 2,890,232 A * | 6/1959 | Rogers, Jr. et al. | 554/75 |
| 3,367,869 A | 2/1968 | Silver et al. | |
| 4,830,838 A | 5/1989 | Kent et al. | |
| 4,871,468 A | 10/1989 | Jeffrey | |
| 5,000,835 A * | 3/1991 | Taylor et al. | 208/39 |
| 5,244,641 A | 9/1993 | Khare | |
| 6,599,472 B1 * | 7/2003 | Hudson | 422/5 |
| 8,034,231 B2 | 10/2011 | Draper | |
| 8,246,813 B2 * | 8/2012 | Compton et al. | 208/239 |
| 2006/0204433 A1 | 9/2006 | Carrette et al. | |
| 2013/0320258 A1 * | 12/2013 | Lehrer et al. | 252/189 |

FOREIGN PATENT DOCUMENTS

| | | | |
|---|---|---|---|
| GB | 1142195 A | 2/1969 | |
| WO | 8201364 A1 | 4/1982 | |
| WO | WO9534524 | * 12/1995 | C07C 53/126 |

OTHER PUBLICATIONS

Andor J.A., et al., Physical and chemical modificaitn of zinc carboxylate-containg lubricants by molecular structure changes, 1999, Lubricaiton Science, 11-2, pp. 115-134.*
Union Camp Corporation, 2000, Carboxylic acids, Fatty acids from Tall oil, Johnson, et al., Kirk-Othmer Encyclopedia of Chemical Technology, Wiley & sons, 4 pages.*
Peterangelo, S. et al., "Correlation between Rheological Properties of Zinc Carboxylate Liquids and Molecular," J. Phys. Chem B. 20078, 111, 7073-7077.

* cited by examiner

*Primary Examiner* — Yate K Cutliff
(74) *Attorney, Agent, or Firm* — Mossman, Kumar & Tyler, P.C.

(57) ABSTRACT

The concentration of hydrogen sulfide in a hydrocarbon can be mitigated by intruding therein a zinc carboxylate oxo complex composition prepared by reacting particulate zinc oxide with a mixture of two or more carboxylic acids wherein the zinc carboxylate oxo complex composition is soluble in hydrocarbons. Useful acids useful include acetic acid, oleic acid, isobutyric acid, lineoleic acid, cekanoic acid, and neodecanoic acid.

13 Claims, No Drawings

OIL SOLUBLE HYDROGEN SULFIDE SCAVENGER

BACKGROUND

1. Field of the Disclosure

The invention relates to the reduction of the concentration of hydrogen sulfide in hydrocarbons. The invention particularly relates scavenging hydrogen sulfide from hydrocarbons.

2. Background of the Disclosure

Hydrogen Sulfide ($H_2S$) is often encountered in the exploration for and production of oil and natural gas. The presence of $H_2S$ is usually objectionable because it may react with other hydrocarbons or fuel system components. Another reason that the $H_2S$ is objectionable is that it may be highly corrosive. Still another reason that $H_2S$ is undesirable is that it is a cause of highly noxious odors.

One solution to these problems is to "scavenge" $H_2S$. Metal based scavengers and certain triazines and aldehydes are known to be useful for these purposes. For example, glyoxal (OHCCHO) has been used at pH neutral as a successful scavenger. Glyoxal and other aldehydes such as acrolein and formaldehyde are known to be useful in a variety of other applications such as biocides, disinfectants, and the like.

But the use of such aldehydes can of themselves sometimes be a problem. Aldehydes may be corrosive to metals such as aluminum, iron, and steel.

Metal Carboxylates are known to be useful for reducing the concentration of hydrogen sulfide in hydrocarbons. Unfortunately, many of the prior art metal carboxylates, especially those prepared with acetic acid, are insoluble in hydrocarbons and must be used as a dispersion or the like. It would be desirable in the art to prepare an oil soluble hydrogen sulfide inhibitor for use with hydrocarbons, especially crude oil, fuel oils, and bitumen.

SUMMARY

In one aspect, the invention is a method for preparing a zinc carboxylate oxo complex composition which is useful for scavenging hydrogen sulfide from a hydrocarbon comprising reacting particulate zinc oxide with a mixture of two or more carboxylic acids wherein: none of the acids is octanoic acid or an octanoic acid isomer, and the zinc carboxylate oxo complex composition is soluble in hydrocarbons.

Another aspect of the invention is a method for preparing a zinc carboxylate oxo complex composition which is useful for scavenging hydrogen sulfide from a hydrocarbon comprising reacting particulate zinc oxide with a mixture of two or more carboxylic acids wherein the a zinc carboxylate oxo complex composition is soluble in hydrocarbons.

In another aspect, the invention is a method for reducing the concentration of hydrogen sulfide in a hydrocarbon comprising introducing a zinc carboxylate oxo complex composition of the disclosure into the hydrocarbon.

DESCRIPTION

In one embodiment, the disclosure is directed to a method for preparing a zinc carboxylate oxo complex composition, useful for scavenging hydrogen sulfide from a hydrocarbon. The zinc carboxylate oxo complex is prepared by reacting particulate zinc oxide with a mixture of two or more carboxylic acids. In this process the carboxylic acids act as both solvent and reactant. The total number of moles of carboxylic acid used in the reaction is equal to about 1.5 times the total moles of zinc added.

This reaction pathway leads to a final zinc product with a zinc to acid ratio of about 2:3. The acids chosen are miscible and of appropriate structure and proportion to result in a product which is uniform and is soluble in organic solvents. The acids may be selected from the group consisting of acetic acid, oleic acid, isobutyric acid, lineoleic acid, cekanoic acid, and neodecanoic acid. In some embodiments, ethyl hexanoic acid may be used while in other embodiments ethyl hexanoic acid is proscribed. The reaction proceeds when the acid mixture is heated as zinc oxide is dissolved in the mixture. The reaction produces the previously mentioned zinc carboxylate oxo complex in addition to water, which is eventually distilled off to purify the zinc carboxylate oxo product.

In some embodiments, the resultant complex can be dissolved in an organic solvent.

Stated another way, the method of the application includes synthesizing a zinc oxo complex of the formula $Zn_4O(acid)_6$ in which the term "acid" refers to a carboxylate ligand with a −1 charge. The carboxylate ligands include two or more differing types of acid ligands and the complex is synthesized using a method in which zinc oxide is reacted neat with a liquid mixture of carboxylic acids. In this embodiment, the combination of acid species as ligands causes the complex to be oil soluble and suitable for injection into hydrocarbon streams whereas a similar complex consisting of only one type of acid ligand would be less suitable for injection or potentially impossible to inject. In each case, the ratio of zinc atoms to total acid ligands in the complex is about 2:3, but the ratio of zinc atoms to each discrete acid ligand may range from about 4:5 to about 4:1 The acid ligands in this embodiment consists of two or more from the types neodecanoic acid, acetic acid, oleic acid, and linoleic acid.

While not wishing to be bound by any theory, it is nevertheless believed that the scavenger remains soluble in the sour hydrocarbon streams due to the highly branched nature of a majority of the ligands bound to the zinc atoms. By synthesizing a complex which is coordinated to a mixture of acid ligands, it is possible to incorporate lower molecular weight acid molecules, allowing an overall lower molecular weight complex. Decreasing the total molecular weight of the oxo zinc complex results in a complex with a higher zinc content by mass, which improves cost effectiveness of the final product with regard to H2S scavenging efficacy. The use of low molecular weight acids does not affect the H2S scavenging efficacy of the product, as the driving force of the scavenging reaction is the production of zinc sulfide and a protonated acid molecule:

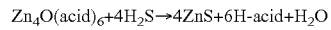

$$Zn_4O(acid)_6 + 4H_2S \rightarrow 4ZnS + 6H\text{-acid} + H_2O$$

The hydrogen sulfide scavengers maybe employed in the process of the disclosure in any way known to be useful to those of ordinary skill in the art of producing oil and gas. For example, it may be atomized and introduced into a gas stream or directly admixed, liquid phase to liquid phase, with a crude oil stream. It may be introduced in a solvent into a viscous phase such as bitumen.

EXAMPLES

The following examples are provided to illustrate the invention. The examples are not intended to limit the scope of the invention and they should not be so interpreted. Amounts are in weight parts or weight percentages unless otherwise indicated.

Example 1

53.2 g of neodecanoic acid and 3.7 g of acetic acid were charged into a reactor, heated to 60° C. and agitated. After reaching temperature, 20 g of zinc oxide powder were slowly added to the acid mixture in small aliquots. Once all the zinc oxide powder was added and dissolved, the temperature of the reactor was increased to 100° C. and agitated for one hour. Following the agitation period, the temperature of the reactor was increased again to 110° C. and a nitrogen sparge was added in order to remove the water entrained in the reaction mixture. Following the collection of water, the reactor temperature was decreased to 80° C., at which point 27.6 g of an aromatic distillate solvent was added and the reaction mixture was allowed to stir for 30 minutes.

Example 2

26.5 g of neodecanoic acid, 9.3 g of acetic acid, and 17.4 g of oleic acid were charged into a reactor, heated to 60° C. and agitated. After reaching temperature, 20 g of zinc oxide powder were slowly added to the acid mixture in small aliquots. Once all the zinc oxide powder was added and dissolved, the temperature of the reactor was increased to 100° C. and agitated for one hour. Following the agitation period, the temperature of the reactor was increased again to 110° C. and a nitrogen sparge was added in order to remove the water entrained in the reaction mixture. Following the collection of water, the reactor temperature was decreased to 80° C., at which point 27.6 g of an aromatic distillate solvent was added and the reaction mixture was allowed to stir for 30 minutes.

Example 3

23.9 g of neodecanoic acid, 10.19 g of acetic acid, and 18 g of oleic acid were charged into a reactor, heated to 60° C. and agitated. After reaching temperature, 20 g of zinc oxide powder was slowly added to the acid mixture in small aliquots. Once all the zinc oxide powder was added and dissolved, the temperature of the reactor was increased to 100° C. and agitated for one hour. Following the agitation period, the temperature of the reactor was increased again to 110° C. and a nitrogen sparge was added in order to remove the water entrained in the reaction mixture. Following the collection of water, the reactor temperature was decreased to 80° C., at which point 27.6 g of an aromatic distillate solvent was added and the reaction mixture was allowed to stir for 30 minutes.

Example 4

26.58 g of neodecanoic acid, 9.27 g of acetic acid, and 17.312 g of linoleic acid were charged into a reactor, heated to 60° C. and agitated. After reaching temperature, 20 g of zinc oxide powder was slowly added to the acid mixture in small aliquots. Once all the zinc oxide powder was added and dissolved, the temperature of the reactor was increased to 100° C. and agitated for one hour. Following the agitation period, the temperature of the reactor was increased again to 110° C. and a nitrogen sparge was added in order to remove the water entrained in the reaction mixture. Following the collection of water, the reactor temperature was decreased to 80° C., at which point 27.6 g of an aromatic distillate solvent was added and the reaction mixture was allowed to stir for 30 minutes.

Examples 5-8 and Comparative Examples A & B

A test is performed using an oxo complex as prepared in Example 1 but with the acids shown in the Table. The additive is introduced at a concentration of 2000 ppm into a hydrocarbon, ISOPAR M (A trademark of EXXON MOBIL CHEMICALS) which has been treated with hydrogen sulfide to have a blank value of 28,000 ppm at 2 hours after treatment and 22,500 ppm at 24 hours after treatment. The results are displayed in the table.

TABLE

| | | Room Temperature 2 Hours Test Fluid Isopar M H2S Blank (ppm) 28,000 | | Room Temperature 24 Hours Test Fluid Isopar M H2S Blank (ppm) 22,500 | |
|---|---|---|---|---|---|
| Sample ID/Product | Soluble (Y/N) | [$H_2S$] | % Reduction | [$H_2S$] | % Reduction |
| Ex 5. Zinc Acetate/ Oleate/ Neodecanoate | Y | 12,000 | 57% | 6,000 | 73% |
| Ex 6 Zinc Acetate/ Neodecanoate | Y | 13,500 | 52% | 8,000 | 64% |
| Ex 7 Zinc Acetate/ Neodecanoate | Y | 12,500 | 55% | 6,500 | 71% |
| Ex 8 Zinc Acetate/ Neodecanoate | Y | 15,000 | 46% | 10,500 | 53% |
| Ex. A Zinc Neodecanoate | Y | 10,500 | 63% | 9,000 | 60% |
| Ex. B Zinc Octoate | N | 11,000 | 61% | 5,000 | 78% |

Discussion of the Examples

The Examples clearly show that an effective and soluble hydrogen sulfide scavenger can be prepared.

The invention claimed is:

1. A method for reducing the concentration of hydrogen sulfide in a hydrocarbon comprising: introducing a zinc carboxylate oxo complex composition into the hydrocarbon; wherein the zinc carboxylate oxo complex is the reaction product from reacting particulate zinc oxide with a mixture of two or more carboxylic acids; wherein the zinc carboxylate oxo complex composition is soluble in hydrocarbons; and wherein none of the acids is octanoic acid or an octanoic isomer.

2. The method of claim 1 wherein at least one of the carboxylic acids is acetic acid.

3. The method of claim 1 wherein a ratio of zinc atoms to total acid ligands in the oxo complex composition is about 2:3.

4. The method of claim 3 wherein a ratio of zinc atoms to each discrete acid ligand may range from about 4:5 to about 4:1.

5. A method for reducing the concentration of hydrogen sulfide in a hydrocarbon comprising: introducing a zinc carboxylate oxo complex composition into the hydrocarbon; wherein the zinc carboxylate oxo complex is the reaction product from:
 mixing two or more carboxylic acids together to form a carboxylic acid mixture; wherein none of the carboxylic acids is octanoic acid or an octanoic isomer; and wherein the two or more carboxylic acids are selected from the group consisting of acetic acid, isobutyric acid, and neodecanoic acid; and reacting particulate zinc oxide with the carboxylic acid mixture to form the zinc carboxylate oxo complex; wherein the zinc carboxylate oxo complex composition is soluble in hydrocarbons.

6. The method of claim 5 wherein at least one of the carboxylic acids is acetic acid.

7. The method of claim 5 wherein a ratio of zinc atoms to total acid ligands in the oxo complex composition is about 2:3.

8. The method of claim 7 wherein a ratio of zinc atoms to each discrete acid ligand may range from about 4:5 to about 4:1.

9. The method of claim 1, wherein at least one of the carboxylic acids is isobutyric acid.

10. The method of claim 5, wherein at least one of the carboxylic acids is isobutyric acid.

11. A method for reducing the concentration of hydrogen sulfide in a hydrocarbon comprising: introducing a zinc carboxylate oxo complex composition into the hydrocarbon; wherein the zinc carboxylate oxo complex is the reaction product from reacting particulate zinc oxide with a mixture of two or more carboxylic acid; wherein the zinc carboxylate oxo complex composition is soluble in hydrocarbons; and wherein none of the acids is octanoic acid or an octanoic isomer, and wherein at least two of the carboxylic acids are neodecanoic acid and isobutyric acid.

12. The method of claim 11 wherein a ratio of zinc atoms to total acid ligands in the oxo complex composition is about 2:3.

13. The method of claim 11 wherein a ratio of zinc atoms to each discrete acid ligand may range from about 4:5 to about 4:1.

* * * * *